United States Patent

Ikeda

(10) Patent No.: US 9,545,109 B2
(45) Date of Patent: Jan. 17, 2017

(54) HERBICIDAL COMPOSITION

(71) Applicant: SUMITOMO CHEMICAL COMPANY, LIMITED, Tokyo (JP)

(72) Inventor: Hajime Ikeda, Kasai (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/471,794

(22) Filed: Aug. 28, 2014

(65) Prior Publication Data

US 2016/0058000 A1 Mar. 3, 2016

(51) Int. Cl.
*A01N 43/84* (2006.01)
*A01N 39/04* (2006.01)
*A01N 33/12* (2006.01)
*A01N 57/20* (2006.01)

(52) U.S. Cl.
CPC ............... *A01N 57/20* (2013.01); *A01N 39/04* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,994,102 A | * | 2/1991 | Yoshido | A01N 57/20 504/128 |
| 2010/0273654 A1 | | 10/2010 | Li et al. | |
| 2011/0105326 A1 | * | 5/2011 | Begliomini | A01N 57/20 504/105 |
| 2014/0179529 A1 | * | 6/2014 | Downer | A01N 57/20 504/128 |
| 2015/0105254 A1 | * | 4/2015 | Li | A01N 37/40 504/105 |

FOREIGN PATENT DOCUMENTS

| | | |
|---|---|---|
| JP | 2-32004 A | 2/1990 |
| WO | WO 2008/106107 A1 | 9/2008 |

OTHER PUBLICATIONS

Meister et al., "The Building Blocks for Global Food Security", Meisterpro Crop Protection Handbook 2012, vol. 98, pp. 7, 442, 452-453, 566-567, 635, 655-656, ISBN: 1-892829-25-8.

* cited by examiner

*Primary Examiner* — John Pak
(74) *Attorney, Agent, or Firm* — Birch, Stewart, Kolasch & Birch, LLP

(57) ABSTRACT

To provide a technology for controlling weeds and the like. A herbicidal composition comprising at least one compound selected from Group A, and 2,4-D choline salt has a weed control effect:

Group A:

a group consisting of flumioxazin, sulfentrazone, saflufenacil, oxyfluorfen, fomesafen and a compound represented by the formula (I):

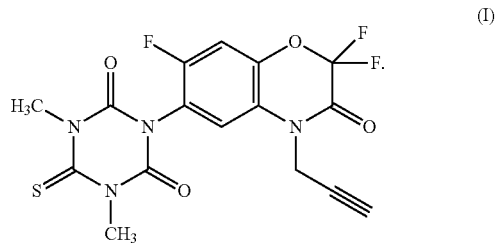

6 Claims, No Drawings

HERBICIDAL COMPOSITION

BACKGROUND OF THE INVENTION

Field of the Invention

The present invention relates to a weed control method.

Description of the Related Art

In order to control weeds, many compounds have been known as an active ingredient of a pest control agent such as a herbicide.

PRIOR ART LITERATURE

Non-Patent Literature

Non-Patent Literature 1: Crop Protection Handbook, vol. 98 (2012) (Meister Publishing Company, ISBN: 1-892829-25-8)

SUMMARY OF THE INVENTION

An object of the present invention is to provide a herbicidal composition having a high control effect on weeds.

The present inventor has found that a specific combination of herbicides has a high control effect on weeds, and the present invention has been completed.

The present invention is as described below.

[1] A herbicidal composition comprising at least one compound selected from Group A, and 2,4-D choline salt, wherein Group A is a group consisting of flumioxazin, sulfentrazone, saflufenacil, oxyfluorfen, fomesafen and a compound represented by the formula (I):

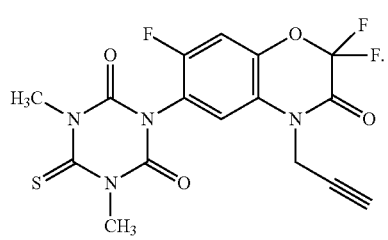

[2] The herbicidal composition according to [1], wherein the weight ratio of the at least one compound selected from Group A to 2,4-D choline salt is from 1:0.2 to 1:200.

[3] The herbicidal composition according to [1], wherein the weight ratio of the at least one compound selected from Group A to 2,4-D choline salt is from 1:0.5 to 1:100.

[4] The herbicidal composition according to [1], which further comprises glyphosate or a salt thereof.

[5] The herbicidal composition according to [4], wherein the weight ratio of the at least one compound selected from Group A to glyphosate or a salt thereof is from 1:0.2 to 1:200 in terms of the weight of glyphosate.

[6] The herbicidal composition according to [4], wherein the weight ratio of 2,4-D choline salt to glyphosate or a salt thereof is from 1:0.05 to 1:20 in terms of the weight of glyphosate.

[7] The herbicidal composition according to any one of [1] to [3], wherein the at least one compound selected from Group A is flumioxazin.

[8] The herbicidal composition according to any one of [4] to [6] wherein the at least one compound selected from Group A is flumioxazin.

A method for controlling weeds, comprising applying at least one compound selected from Group A and 2,4-D choline salt to weeds or soil in a place where the weeds grow or will grow, wherein Group A is a group consisting of flumioxazin, sulfentrazone, saflufenacil, oxyfluorfen, fomesafen and a compound represented by the formula (I):

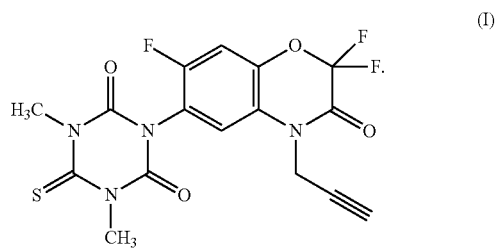 [SMILES: C#CCN1C(=O)C(F)(F)Oc2cc(F)c(-n3c(=O)n(C)c(=S)n(C)c3=O)cc21]

[10] The method according to [9], wherein the weight ratio of the at least one compound selected from Group A to 2,4-D choline salt, is from 1:0.2 to 1:200.

[11] The method according to [9], wherein the weight ratio of the at least one compound selected from Group A to 2,4-D choline salt is from 1:0.5 to 1:100.

[12] The method according to [9], applying the at least one compound selected from Group A, 2,4-D choline salt and glyphosate or a salt thereof.

[13] The method according to [12], wherein the weight ratio of the at least one compound selected from Group A to glyphosate or a salt thereof is from 1:0.2 to 1:200 in terms of the weight of glyphosate.

[14] The method according to [12], wherein the weight ratio of 2,4-D choline salt to glyphosate or a salt thereof is in a range of from 1:0.05 to 1:20 in terms of the weight of glyphosate.

[15] The method according to any one of [9] to [14], wherein the place where the weeds grow or will grow is a soybean field, a cotton field, or a corn field.

[16] The method according to [15], wherein a soybean in the soybean field, cotton in the cotton field or corn in the corn field is a genetically-modified soybean, genetically-modified cotton or genetically-modified corn.

[17] The method according to [15], wherein a soybean in the soybean field, cotton in the cotton field or corn in the corn field is a herbicide-resistant genetically-modified soybean, herbicide-resistant genetically-modified cotton or herbicide-resistant genetically-modified corn.

[18] The method according to [15], wherein a soybean in the soybean field or cotton in the cotton field is a 2,4-D-resistant genetically-modified soybean or 2,4-D-resistant genetically-modified cotton.

[19] The method according to any one of [9] to [11], wherein the at least one compound selected from Group A is flumioxazin.

[20] The method according to any one of [12] to [18], wherein the at least one compound selected from Group A is flumioxazin.

According to the present invention, it is possible to control weeds with a high effect.

DETAILED DESCRIPTION OF THE PREFERRED EMBODIMENTS

A herbicidal composition of the present invention (hereinafter, referred to as the composition of the present invention) comprises at least one compound selected from Group A, and 2,4-D choline salt:

Group A;
a group consisting of flumioxazin, sulfentrazone, saflufenacil, oxyfluorfen, fomesafen and a compound represented by the formula (I):

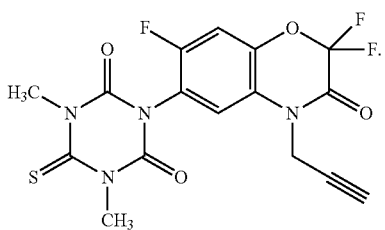

The composition of the present invention comprises at least one compound selected from Group A as a first component:
Group A;
a group consisting of flumioxazin, sulfentrazone, saflufenacil, oxyfluorfen, fomesafen and a compound represented by the formula (I) (hereafter described as Compound 1):

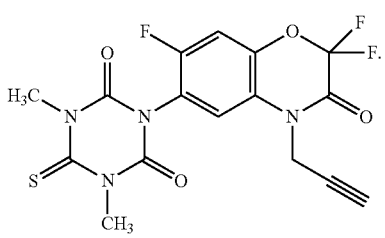

Flumioxazin, sulfentrazone, saflufenacil, oxyfluorfen, and fomesafen are well known herbicidal active compounds and described in Crop Protection Handbook, vol. 98 (2012) (Meister Publishing Company, ISBN: 1-892829-25-8), and can be produced by the known processes, and commercially available preparations containing them can be obtained.

Fomesafen used in the present invention may be a salt such as fomesafen-sodium.

Compound 1 is a herbicidal active compound described in WO 10/145992 and can be produced by a method described in this publication.

The composition of the present invention comprises 2,4-D choline salt as a second component.

2,4-D choline salt is a herbicide described in WO 08/106107 and can be produced by a method described in this publication. In the case of referring to 2,4-D in the present invention, the 2,4-D refers to a form of an acid of 2,4-D.

The composition of the present invention may also comprise glyphosate or a salt thereof as a third component.

Glyphosate or a salt thereof used in the present invention may be either in a form of an acid of glyphosate, or a form of a salt of glyphosate, and a form of a salt of glyphosate is usually used.

Specific examples of the salt of glyphosate include glyphosate isopropylamine salt, glyphosate-trimethylsulfonium, glyphosate-ammonium, glyphosate-diammonium, glyphosate-sodium, glyphosate-potassium, glyphosate guanidine derivative salts, glyphosate choline salt and glyphosate N,N-Bis (3-aminopropyl)methylamine salt. These salts of glyphosate are described in Crop Protection Handbook, vol. 98 (2012) (Meister Publishing Company, ISBN: 1-892829-25-8), Compendium of Pesticide Common Names (http://www.alanwood.net/pesticides/), U.S. Pat. No. 3,799, 758, WO 08/106107, WO 11/008453 and WO 11/039172, and they can be produced by a known production method.

In the case of referring to glyphosate in the present invention, the glyphosate refers to a form of an acid of glyphosate.

The composition of the present invention has herbicidal activity against a wide variety of weeds, and thus enabling effective control of a wide variety of weeds in the fields where crops are usually cultivated with or without tillage, vegetable field, tree land or non-cultivated land.

Examples of the farm crop field in the present invention include fields of edible crops such as peanut, soybean, corn, wheat and barley; feed crops such as sorghum and oat; industrial crops such as cotton; and sugar crops such as sugarcane. Examples of the vegetable field in the present invention include fields of Solanaceae vegetables such as eggplant, tomato, green pepper, red pepper and potato; Cucurbitaceae vegetables such as cucumber, pumpkin, zucchini, watermelon and melon; Brassicaceae vegetables such as radish, turnip, horseradish, cohlrabi, Chinese cabbage, cabbage, leaf mustard, broccoli and cauliflower; Compositae vegetables such as burdock, crown daisy, artichoke and lettuce; Liliaceae vegetables such as leek, onion, garlic and asparagus; Umbelliferae vegetables such as carrot, parsley, celery and parsnip; Chenopodiaceae vegetables such as spinach and Swiss chard; Lamiacea vegetables such as perilla, mint, basil and lavender; strawberry; sweet potato; yam; and taro.

Examples of the tree land in the present invention include orchards, tea plantation, mulberry field, coffee plantation, banana plantation, palm plantation, flower tree land, flower field, nursery tree land, young plant land, forest and garden. Examples of the orchard include pome fruits such as apple, pear, Japanese pear, Chinese quince and quince; stone fruits such as peach, plum, nectarine, Japanese apricot, cherry, apricot and prune; citrus such as Satsuma orange, orange, lemon, lime and grapefruit; tree nuts such as chestnut, walnut, hazelnut, almond nut, pistachio nut, cashew nut and macadamia nut; berries such as blueberry, cranberry, blackberry and raspberry; grape; persimmon; olive; and loquat.

Examples of the non-cultivated land in the present invention include playground, vacant land, neighborhood of railroad, park, car park, neighborhood of road, dry riverbed, land under power-transmission lines, land for housing and site for factor.

Crops cultivated in the farm crop field in the present invention are not limited as long as they belong to cultivars which are generally cultivated as crops.

These plant, cultivars include plants, to which resistance to herbicides has been imparted by a classical breeding method or genetic recombination technology, the herbicides being protoporphyrinogen oxidase inhibitors such as flumioxazin; 4-hydroxyphenylpyruvate dioxygenase inhibitors such as isoxaflutole; acetolactate synthase inhibitors such as imazethapyr and thifensulfuron-methyl; acetyl CoA carboxylase inhibitors such as sethoxydim; 5-enolpyruvyishikimate-3-phosphate synthase inhibitors such as glyphosate; glutamine synthetase inhibitors such as glufosinate; auxin type herbicides such as 2,4-D and dicamba; and bromoxynil.

Examples of the crop, to which resistance to herbicides has been imparted by a classical breeding method, include corn which is resistant to an imidazolinone type acetolactate synthase inhibiting herbicide such as imazethapyr, and which has already been sold under the trade name of Clearfield (registered trademark). Such a crop also includes STS soybean which is resistant to a sulfonylurea type acetolactate synthase inhibiting herbicide such as thifensulfuron-methyl. Similarly, examples of the plant, to which resistance to an acetyl CoA carboxylase inhibitor such as a trione oxime or aryloxyphenoxypropionic acid type herbicide has been imparted by a classical breeding method, include SR corn.

Examples of the plant, to which resistance to herbicides has been imparted by genetic recombination technology, include corn, soybean and cotton, each having resistance to glyphosate, and which have already been sold under the trade names of RoundupReady (registered trademark), Agrisure (registered trademark) GT, and Gly-Tol (registered trademark). Similarly, plants, to which resistance to herbicides has been imparted by genetic recombination technology, include corn, soybean and cotton, each having resistance to glufosinate, and they have already been sold under the trade name of LibertyLink (registered trademark). There are corn and soybean cultivars, which are resistant to both glyphosate and ALS inhibitors, and are sold under the trade name of Optimum (registered trademark) GAT (registered trademark). Similarly, there is soybean, to which resistance to an imidazolinone type acetolactate synthase inhibitor has been imparted by genetic recombination technology, and which has been developed under the trade name of Cultivance. Similarly, there is cotton, to which resistance to bromoxynil has been imparted by genetic recombination technology, and which has already been sold under the trade name of BXN (registered trademark). There is soybean, which is resistant to both glyphosate and dicamba, and has been developed under the brand of RoundupReady (registered trademark) 2 Xtend. Similarly there is cotton, which resistant to both glyphosate and dicamba.

Crops having resistance to both phenoxy acid type herbicides such as 2,4-D, MCPA, dichlorprop and mecoprop, and aryloxyphenoxypropionic acid type herbicides such as quizalofop, haloxyfop, fluazifop, diclofop, fenoxaprop, metamifop, cyhalofop and clodinafop can be fabricated by introducing a gene encoding an aryloxyalkanoate dioxygenase (Wright et al. 2010: Proceedings of National Academy of Science. 107 (47): 20240-20245). Cultivars of soybean and cotton, which show the resistance to 2,4-D, have been developed under the brand of Enlist.

By introducing a gene encoding a 4-hydroxyphenylpyruvate dioxygenase (hereinafter referred to as HPPD) inhibitor which exhibits resistance to HPPD inhibitor, and thus plants having resistance to the HPPD inhibitor can be fabricated (U.S. 2004/0058427). By introducing a gene capable of synthesizing homogentisic acid as a product of HPPD through another metabolic pathway, homogentisic acid is produced even in the presence of a HPPD inhibitor, and thus making it possible to fabricate plants which exhibits resistance to the HPPD inhibitor (WO 02/036787). By introducing a gene capable of excessively expressing HPPD, HPPD is produced in the amount which does not exert an adverse influence on the growth of the plant even in the presence of a HPPD inhibitor, and thus making it possible to fabricate plants which exhibit resistance to the HPPD inhibitor (WO 96/38567). By introducing aforementioned gene capable of excessively expressing HPPD and also introducing a gene encoding a prephenate dehydrogenase so as to increase the production amount of p-hydroxyphenylpyruvic acid as a substrate of HPPD, and thus making it possible to fabricate plants which exhibit resistance to the HPPD inhibitor (Rippert P et al. 2004 Engineering plant shikimate pathway for production of tocotrienol and improving herbicide resistance. Plant Physiol. 134: 92-100).

Examples of the other method of imparting resistance to a herbicide include methods of introducing genes described in WO 98/20144, WO 02/46387 and U.S. 2005/0246800.

Aforementioned crops also include crops which made it possible to synthesize selective toxins known as the genus Bacillus, using genetic recombination technology.

Examples of toxins expressed in these transgenic plants include insecticidal proteins derived from Bacillus cereus and Bacillus popilliae*; δ-endotoxins derived from *Bacillus thuringiensis*, e.g. Cry1Ab, Cry1Ac, Cry1F, Cry1Fa2, Cry2Ab, Cry3A, Cry3Bb1 and Cry9C , Cry34ab and Cry35ab, and insecticidal proteins such as VTP1, VIP2 , VIP3 and VTP3A; insecticidal toxins derived from nematodes; insecticidal toxins produced by animals, such as scorpion toxin, spider toxin, bee toxin and insect-specific neurotoxins; filamentous fungi toxins; plant lectins; agglutinin; protease inhibitor such as trypsin inhibitor, serine protease inhibitor, patatin, cystatin and papain inhibitor; ribosome-inactivating proteins (RIP) such as ricin, corn-RIP, abrin, rufin, sapolin and priodin; steroid metabolic enzymes such as 3-hydroxysteroid oxidase ecdysteroid-UDP-glucosyltransferase and cholesterol oxidase; ecdysone inhibitor; HMG-CoA reductase; ion channel inhibitors such as sodium channel inhibitor and calcium channel inhibitor; juvenile hormone esterase; diuretic hormone acceptors; stilbene synthetase; bibenzyl synthetase; chitinase; and glucanase.

The toxins expressed in these transgenic plants include hybrid toxins, partially deficient toxins and modified toxins, which derive from δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and insecticidal proteins such as VTP1, VIP2, VIP3 and VIP3A. The hybrid toxins are fabricated by a novel combination of the different domains of these proteins, using genetic recombination technology. The known partially deficient toxin is Cry1Ab, in which a part of amino acid sequence is deficient. In modified toxins, one or more amino acids of a natural toxin are replaced. Examples of these toxins and transgenic plants capable of synthesizing these toxins are described in EP-A-0 374 753, WO 93/07278, WO 95/34656, EP-A-0 427 529, EP-A-451 878, and WO 03/052073. The toxins contained in these transgenic plants impart resistance to insect pests of Coleoptera, insect pests of Diptera and insect pests of Lepidoptera to the plants.

There have already been known transgenic plants having one or more insecticidal pest-resistant genes and capable of producing one or more toxins, and some of them are commercially available. Examples of the transgenic plants include YieldGard (registered trademark) (a corn variety expressing Cry1Ab toxin), YieldGard Rootworm (registered trademark) (a corn variety expressing Cry3Bb1 toxin), YieldGard Plus (registered trademark) (a corn variety expressing Cry1Ab and Cry3Bb1 toxins), Herculex I (registered trademark) (a corn variety expressing Cry1Fa2 toxin and phosphinothricin N-acetyltransferase (PAT) to impart resistance to glufosinate), NatureGard (registered trademark), AGRISURE (registered trademark) CB Advantage (Bt11 corn borer (CB) character), and Protecta (registered trademark).

There have already been known transgenic cottons having one or more insecticidal pest-resistant genes and capable of producing one or more toxins, and some of them are commercially available. Examples of the transgenic cottons include BollGard (registered trademark) (cotton cultivar expressing a Cry1Ac toxin), BollGard (registered trademark) II (cotton cultivar expressing Cry1Ac and Cry2Ab toxins), BollGard (registered trademark) III (cotton cultivar expressing Cry1Ac, Cry2Ab and VTP3A toxins), VipCot (registered trademark) (cotton cultivar expressing a VIP3A and Cry1Ab toxins) and WideStrike (registered trademark) (cotton cultivar expressing Cry1Ac and Cry1F toxins).

Examples of the plant used in the present invention include plants imparted with resistance to aphids, such as soybean having a Rag1 (Resistance Aphid Gene1) gene introduced thereto.

The above crops also include those imparted with a capacity of producing an anti-pathogenic substance having selective activity. As the anti-pathogenic substance, PR proteins (PRPs, EP-A-0 392 225) are known. These anti-pathogenic substances and transgenic plants producing thereof are described in EP-A-0 392 225, WO 95/33818, and EP-A-0 353 191. Examples of the anti-pathogenic substance expressed by the transgenic plants include ion channel inhibitors such as a sodium channel inhibitor and calcium channel inhibitor (KP1, KP4 and KP6 toxins produced by viruses are known); stilbene synthases; bibenzyl synthases; chitinase; glucanase; PR proteins; and substances produced by microorganisms, such as peptide antibiotics, antibiotics having a heterocyclic ring and protein factors (called genes resistant to plant diseases and are described in WO 03/000906) involved in plant disease resistance.

The above crops include those imparted with useful traits, such as reformed oil component and enhanced amino acid content, by means of a genetic recombination technique. The crops are exemplified by VISTIVE (registered trademark) (low linolenic soybean with reduced linolenic acid content) and high-lysine (high-oil) corn (corn with increased lysine or oil content).

The crops further include stacked varieties, which are fabricated by combining the above classical herbicidal traits or herbicide resistant genes, insecticidal pest resistant genes, anti-pathogenic substance-producing genes, reformed oil component and enhanced amino acid content.

The above-mentioned crops include those imparted with tolerance to diseases, tolerance to dehydration stresses, traits to increase sugar content, and so on.

The composition of the present invention can control weeds effectively in, especially, soybean fields, cotton fields, and corn fields.

Examples of weeds capable of controlling the composition of the present invention include the followings:

Urticaceae weeds: *Urtica urens*

Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius, Rumex acetosa*

Portulacaceae weeds: *Portulaca oleracea*

Caryophyllaceae weeds: *Stellaria media, Cerastium holosteoides, Cerastium glomeratum, Spergula arvensis, Silene gallica*

Aizoaceae weeds: *Mollugo verticillata*

Chenopodiaceae weeds: *Chenopodium album, Chenopodium ambrosioides, Kochia scoparia, Salsola kali, Atriplex* spp.

Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Amaranthus deflexus, Amaranthus quitensis, Alternanthera philoxeroides, Alternanthera sessilis, Alternanthera tenella*

Papaveraceae weeds: *Papaver rhoeas, Argemone mexicana*

Brassicaceae weeds: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum, Coronopus didymus*

Capparaceae weeds: *Cleome affinis*

Fabaceae weeds: *Aeschynomene indica, Aeschynomene rudis, Sesbania exaltata, Cassia obtusifolia, Cassia occidentalis, Desmodium tortuosum, Desmodium adscendens, Trifolium repens, Pueraria lobata, Vicia angustifolia, Indigofera hirsuta, Indigofera truxillensis, Vigna sinensis*

Oxalidaceae weeds: *Oxalis corniculata, Oxalis strica, Oxalis oxyptera*

Geraniaceae weeds: *Geranium carolinense, Erodium cicutarium*

Euphorbiaceae weeds: *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis, Ricinus communis*

Malvaceae weeds: *Abutilon theophrasti, Sida rhombifolia, Sida cordifolia, Sida spinosa, Sida glaziovii, Sida santaremnensis, Hibiscus trionum, Anoda cristata, Malvastrum coromandelianum*

Sterculiaceae weeds: *Waltheria indica*

Violaceae weeds: *Viola arvensis, Viola tricolor*

Cucurbitaceae weeds: *Sicyos angulatus, Echinocystis lobata, Momordica charantia*

Lythraceae weeds: *Lythrum salicaria*

Apiaceae weeds: *Hydrocotyle sibthorpioides*

Sapindaceae weeds: *Cardiospermum halicacabum*

Primulaceae weeds: *Anagallis arvensis*

Asclepiadaceae weeds: *Asclepias syriaca, Ampelamus albidus*

Rubiaceae weeds: *Galium aparine, Galium spurium* var. *echinospermon, Spermacoce latifolia, Richardia brasiliensis, Borreria alata*

Convolvulaceae weeds: *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides, Jacquemontia tamnifolia*

Boraginaceae weeds: *Myosotis arvensis*

Lamiaceae weeds: *Lamium purpureum, Lamium amplexicaule, Leonotis nepetaefolia, Hyptis suaveolens, Hyptis lophanta, Leonurus sibiricus, Stachys arvensis*

Solanaceae weeds: *Datura stramonium, Solarium nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata, Nicandra physaloides*

Scrophulariaceae weeds: *Veronica hederaefolia, Veronica persica, Veronica arvensis*

Plantaginaceae weeds: *Plantago asiatica*

Asteraceae weeds: *Xanthium pensylvanicum, Xanthium occidentale, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum offi-* cinale, Galinsoga ciliata, Galinsoga parviflora, Senecio vulgaris, Senecio brasiliensis, Senecio grisebachii, Conyza bonariensis, Conyza canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis Liliaceae weeds: *Allium canadense, Allium vineale*

Commelinaceae weeds: *Commelina communis, Commelina bengharensis, Commelina erecta*

Poaceae weeds: *Echinochloa crus-galli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spicaventi, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Oryza sativa, Paspalum notatum, Paspalum maritimum, Pennisetum clandestinum, Pennisetum setosum, Rottboellia cochinchinensis*

Cyperaceae weeds: *Cyperus microiria, Cyperus iria, Cyperus odoratus, Cyperus rotundus, Cyperus esculentus, Kyllinga gracillima*

Equisetaceae weeds: *Equisetum arvense, Equisetum palustre.*

In the composition of the at least one compound selected from Group A, and 2,4-D choline salt in the present invention, the weight ratio of the at least one compound selected from Group A to 2,4-D choline salt is usually from 1:0.01 to 1:600, preferably from 1:0.2 to 1:200, more preferably from 1:0.5 to 1:100, and still more preferably 1:2.5 to 1:80.

In the composition of the at least one compound selected from Group A, 2,4-D choline salt and glyphosate or a salt thereof in the present invention, the weight ratio of the at least one compound selected from Group A to glyphosate or a salt thereof is usually from 1:0.01 to 1:600, preferably from 1:0.2 to 1:200, and more preferably from 1:0.5 to 1:100, in terms of the weight of glyphosate.

In the composition of the at least one compound selected from Group A, 2,4-D choline salt and glyphosate or a salt thereof in the present invention, the weight ratio of 2,4-D choline salt to glyphosate or a salt thereof is usually from 1:0.001 to 1:100, preferably from 1:0.05 to 1:20, in terms of the weight of glyphosate.

In the composition of the at least one compound selected from Group A, 2,4-D choline salt and glyphosate or a salt thereof in the present invention, the weight ratio of the at least one compound from Group A: 2,4-D choline salt: glyphosate or a salt thereof is preferably 1:0.2-200:0.2-200, in terms of the weight of glyphosate.

Usually, the composition of the present invention is formulated to emulsifiable concentrates, wettable powders, suspensible concentrates, granules, and so on by being mixed with a solid carrier, a liquid carrier, or the like, and optionally with surfactants and other auxiliaries for formulation. These formulations generally contain 0.1 to 90% by weight, preferably about 1 to about 80% by weight of the total amount of the at least one compound selected from Group A, and 2,4-D choline salt.

Also when the composition of the present invention further comprises glyphosate or a salt thereof, these formulations generally contain 0.1 to 90% by weight, preferably about 1 to about 80% by weight of the total amount of the at the least one compound selected from Group A, 2,4-D choline salt and glyphosate or a salt thereof.

Examples of the solid carrier used for formulating the composition of the present invention include fine powders and granules of clays such as kaolinite, diatomaceous earth, synthetic hydrated silica, Fubasami clay, bentonite and acid clay; talc; other inorganic minerals such as sericite, quartz powder, sulfur powder, activated carbon and calcium carbonate; and chemical fertilizer such as ammonium sulfate, ammonium phosphate, ammonium nitrate, ammonium chloride and urea. Examples of the liquid carrier include water; alcohols such as methanol and ethanol; ketones such as acetone, methyl ethyl ketone and cyclohexanone; aromatic hydrocarbons such as toluene, xylene, ethylbenzene and methylnaphthalene; non-aromatic hydrocarbons such as hexane, cyclohexane and kerosene; esters such as ethyl acetate and butyl acetate; nitriles such as acetonitrile and isobutyronitrile; ethers such as dioxane and diisopropyl ether; acid amides such as dimethylformamide and dimethylacetamide; and halogenated hydrocarbons such as dichloroethane and trichloroethylene.

Examples of the surfactant used for formulating the composition of the present invention include alkyl sulfate esters, alkylsulfonate salts, alkylarylsulfonate salts, alkylaryl ethers, polyoxyethylene alkylaryl ethers, polyethylene glycol ethers, polyhydric alcohol esters and sugar alcohol derivatives. Examples of the other auxiliary for formulation include sticking agents and dispersants, such as casein; gelatin; polysaccharides such as starch, gum arabic, cellulose derivatives and alginic acid; lignin derivatives; bentonite; and synthetic water-soluble polymers such as polyvinyl alcohol, polyvinylpyrrolidone and polyacrylic acid; and stabilizers such as PAP (isopropyl acid phosphate), BHT (2,6-tert-butyl-4-methylphenol), BHA (2-/3-tert-butyl-4-methoxyphenl), vegetable oil, mineral oil, fatty acid and fatty acid ester.

The composition of the present invention can also be prepared by formulating each of the active ingredients by the above-described procedure, and then mixing the resulting formulations.

The formulated composition of the present invention can be applied as it is to a soil or a plant or alternatively may be applied to a soil or a plant after being diluted with water or the like. Moreover, the composition of the present invention may be used for increasing herbicidal activities by being used in admixture with another herbicide. Furthermore, the composition of the present invention can be used together with insecticides, fungicides, plant growth regulators, fertilizers, soil-improving agents, and so on.

Examples of herbicides with which the composition of the present invention may be mixed include the following.

2,4-DB, 2,4-DB-dimethylammonium, 2,4-DB-isooctyl, 2,4-DB-butyl, 2,4-DB-sodium, 2,4-DB-potassium, 2,4-DB choline salt, 2,4-DB-N, N-bis-(3-aminopropyl) methylamine salt, MCPA, MCPA-dimethylammonium, MCPA-2-ethylhexyl, MCPA-isooctyl, MCPA-butotyl, MCPA-butyl, MCPA diolamine salt, MCPA-ethyl, MCPA-isobutyl, MCPA-isopropyl, MCPA-methyl, MCPA olamine salt, MCPA-sodium, MCPA trolamine salt, MCPA choline salt, MCPA N, N-bis-(3-aminopropyl)methylamine salt, MCPB, MCPB-ethyl, MCPB-methyl, MCPB-sodium, MCPB choline salt, MCPB N, N-bis-(3-aminopropyl)methylamine salt, mecoprop, mecoprop-dimethylammonium, mecoprop diolamine salt, mecoprop-ethadyl, mecoprop-2-ethylhexyl, mecoprop-isooctyl, mecoprop-methyl, mecoprop-potassium, mecoprop-sodium, mecoprop trolamine salt, mecoprop choline salt, mecoprop-P, mecoprop-P-dimethylammonium, mecoprop-P-2-ethylhexyl, mecoprop-P-isobutyl, mecoprop-P-potassium, mecoprop-P choline salt, mecoprop N, N-bis-(3-aminopropyl)methylamine salt, dichlorprop, dichlorprop-butotyl, dichlorprop-dimethylammonium, dichlorprop-ethylammonium, dichlorprop-2-ethylhexyl, dichlorprop-isooctyl, dichlorprop-methyl, dichlorprop-potassium, dichlorprop-sodium, dichlorprop choline salt, dichlorprop N, N-bis-(3-aminopropyl)methylamine salt, dichlorprop-P, dichlorprop-P-dimethylammonium, dichlorprop-P-2-ethylhexyl, dichlorprop-P choline salt, dichlorprop-P N,N-bis-(3-aminopropyl)methylamine salt, dicamba, dicamba diglycolamine salt, dicamba-dimethylammonium, dicamba diolamine salt, dicamba-isopropylammonium, dicamba-methyl, dicamba olamine salt, dicamba-potassium, dicamba-sodium, dicamba trolamine salt, dicamba choline salt, dicamba N, N-bis-(3- aminopropyl)methylamine salt, bromoxynil, bromoxynil-octanoate, dichlobenil, ioxynil, ioxynil-octanoate, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, aminocyclopyrachlor-methyl, aminocyclopyrachlor-potassium, trifluralin, pendimethalin, ethalfluralin, benfluralin, prodiamine, simazine, atrazine, propazine, cyanazine, ametryn, simetryn, dimethametryn, procmetryn, indaziflam, triaziflam, metribuzin, hexazinone, isoxaben, diflufenican, diuron, linuron, fluometuron, difenoxuron, metnyldymron, isoproturon, isouron, tebuthiuron, benzthiazuron, methabenzthiazuron, propanil, mefenacet, clomeprop, naproanilide, bromobutide, daimuron, cumyluron, etobenzanid, bentazon, tridiphane, indanofan, amitrole, fenchiorazole, clomazone, maleic hydrazide, pyridate, chloridazon, norflurazon, bromacil, terbacil, oxaziclomefone, cinmethylin, benfuresate, cafenstrole, carfentrazone-ethyl, flumiclorac-pentyl, pyrithiobac, pyrithiobac-sodium, pyriminobac, pyriminobac-methyl, bispyribac, bispyribac-sodium, pyribenzoxim, pyrimisulfan, pyriftalid, triafamone, fentrazamide, dimethenamid, dimethenamid-P, ACN, benzobicyclon, dithiopyr, triclopyr, triclopyr-butotyl, triclopyr-ethyl, triclopyr-triethylammonium, thiazopyr, fluroxypyr, fluroxypyr-meptyl, aminopyralid, aminopyralid-potassium, aminopyralid-tris(2-hydroxypropyl)ammonium), aminopyralid-choline, clopyralid, clopyralid-methyl, clopyralid-olamine, clopyralid-potassium, clopyralid-tris(2-hydroxypropyl)ammonium, clopyralid-choline, dalapon, chlorthiamid, amidosulfuron, azimsulfuron, bensulfuron, bensulfuron-methyl, chlorimuron, chlorimuron -ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, mesotrione, sulcotrione, tefuryltrione, tembotrione, isoxaflutole, isoxachlortole, benzofenap, pyrasulfotole, pyrazolynate, pyrazoxyfen, topramezone, flupoxam, amicarbazone, bencarbazone, flucarbasone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazaquin, imazethapyr, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glufosinate, glufosinate-ammonium, glufosinate-P, glufosinate-P-sodium, glufosinate-P-ammonium, bialafos, anilofos, bensulide, butamifos, paraquat, paraquat-dichloride, diquat and diquat-dibromide.

The application amount of the composition of the present invention can be changed depending on the mixing ratio of the at least one compound selected from Group A, and 2,4-D choline salt, weather conditions, formulation types, application time, application methods, application places, weeds to be controlled and objective crops, however, it is usually 100 to 4000 g based on the total amount of the at least one compound selected from Group A, and 2,4-D choline salt per hectare.

Also when the composition of the present invention further comprises glyphosate or a salt thereof, it is usually 100 to 4000 g based on the total amount of the at least one compound selected from Group A, 2,4-D choline salt and glyphosate or a salt thereof per hectare.

Emulsifiable concentrates, wettable powders, suspensions and the like are generally diluted with 100 to 2000 liters of water per hectare so as to be the above-described amount of the active ingredients (i.e. the at least one compound selected from Group A, 2,4-D choline salt and optionally glyphosate or a salt thereof), and then applied. In addition, when weeds are subjected to foliar treatment with the composition of the present invention, an increase of the effect on weeds can be expected by adding an adjuvant to a diluent of the composition of the present invention.

In the method for controlling weeds of the present invention, the composition of the present invention is applied to weeds or a place where weeds are to emerge. The application to weeds may be application to weeds per se or application to a soil where weeds have emerged. The application to a place where weeds are to emerge may be application to the surface of a soil where weeds have not emerged yet.

In the method for controlling weeds of the present invention, the at least one compound selected from Group A, and 2,4-D choline salt are applied in an above-described weight ratio.

In the method for controlling weeds of the present invention, when the at least one compound selected from Group A, 2,4-D choline salt and glyphosate or a salt thereof are applied, the at least one compound selected from Group A, 2,4-D choline salt and glyphosate or a salt thereof are applied in an above-described weight ratio.

Examples of the application method of the composition of the present invention include the following embodiments: a method of applying the composition of the present invention over the surface of a soil before sowing seeds of crops and before weed emergence;
a method of applying the composition of the present invention over the surface of a soil before sowing seeds of crops and after weed emergence;
a method of applying the composition of the present invention over weeds before sowing seeds of crops and after weed emergence;
a method of applying the composition of the present invention over a surface of the soil after sowing seeds of crops, before emergence of the crops, and before weed emergence;
a method of applying the composition of the present invention over the surface of a soil after sowing seeds of crops, before emergence of the crops, and after weed emergence;
a method of applying the composition of the present invention over weeds after sowing seeds of crops, before emergence of the crops, and after weed emergence;
a method of applying the composition of the present invention over the surface of a soil in the presence of crops, before weed emergence;
a method of applying the composition of the present invention over the surface of a soil in the presence of crops, after weed emergence; and/or
a method of applying the composition of the present invention over weeds in the presence of crops, after weed emergence.

EXAMPLES

Hereinbelow, the present invention will be described by way of examples, but the present invention is not limited to these examples.
[Formulation]
Formulation examples are shown below.
Formulation examples are shown below. In the following examples, parts are all parts by weight.

Formulation Example 1

Flumioxazin (0.2 parts), 2,4-D choline salt (4 parts), polyoxyethylene steryl phenyl ether (14 parts), calcium dodecylbenzenesulfonate (6 parts), xylene (30 parts) and N,N-dimethylformamide (45.8 parts) are mixed to obtain an emulsifiable concentrate.

Formulation Example 2

Flumioxazin (1 part), 2,4-D choline salt (2.5 parts), polyoxyethylene steryl phenyl ether (14 parts), calcium dodecylbenzenesulfonate (6 parts), xylene (30 parts) and N,N-dimethylformamide (46.5 parts) are mixed to obtain an emulsifiable concentrate.

Formulation Example 3

Flumioxazin (0.7 parts), 2,4-D choline salt (10 parts), polyoxyethylene steryl phenyl ether (14 parts), calcium dodecylbenzenesulfonate (6 parts), xylene (30 parts) and N,N-dimethylformamide (39.3 parts) are mixed to obtain an emulsifiable concentrate.

Formulation Example 4

Flumioxazin (0.125 parts), 2,4-D choline salt (10 parts), polyoxyethylene steryl phenyl ether (14 parts), calcium dodecylbenzenesulfonate (6 parts), xylene (30 parts) and N,N-dimethylformamide (39.875 parts) are mixed to obtain an emulsifiable concentrate.

Formulation Example 5

Flumioxazin (0.14 parts), 2,4-D choline salt (2 parts), glyphosate potassium salt (2 parts), polyoxyethylene steryl phenyl ether (14 parts), calcium dodecylbenzenesulfonate (6 parts), xylene (30 parts) and N,N-dimethylformamide (45.86 parts) are mixed to obtain an emulsifiable concentrate.

Formulation Example 6

Flumioxazin (0.14 parts), 2,4-D choline salt (2 parts), glyphosate isopropylamine salt (2 parts), polyoxyethylene steryl phenyl ether (14 parts), calcium dodecylbenzenesulfonate (6 parts), xylene (30 parts) and N,N-dimethylformamide (45.86 parts) are mixed to obtain an emulsiliable concentrate.

Formulation Example 7

Flumioxazin (0.2 parts), 2,4-D choline salt (4 parts), glyphosate potassium salt (4 parts), polyoxyethylene steryl phenyl ether (14 parts), calcium dodecylbenzenesulfonate (6 parts), xylene (30 parts) and N,N-dimethylformamide (41.8 parts) are mixed to obtain an emulsifiable concentrate.

Formulation Example 8

Flumioxazin (0.2 parts), 2,4-D choline salt (4 parts), glyphosate isopropylamine salt (4 parts), polyoxyethylene steryl phenyl ether (14 parts), calcium dodecylbenzenesulfonate (6 parts), xylene (30 parts) and N,N-dimethylformamide (41.8 parts) are mixed to obtain an emulsifiable concentrate.

Formulation Example 9

Flumioxazin (0.2 parts), 2,4-D choline salt (2 parts), glyphosate potassium salt (4 parts), polyoxyethylene steryl phenyl ether (14 parts), calcium dodecylbenzenesulfonate (6 parts), xylene (30 parts) and N,N-dimethylformamide (43.8 parts) are mixed to obtain an emulsifiable concentrate.

Formulation Example 10

Flumioxazin (0.2 parts), 2,4-D choline salt (4 parts), glyphosate potassium salt (2 parts), polyoxyethylene steryl phenyl ether (14 parts), calcium dodecylbenzenesulfonate (6 parts), xylene (30 parts) and N,N-dimethylformamide (43.8 parts) are mixed to obtain an emulsifiable concentrate.

Formulation Example 11

Flumioxazin (0.2 parts), 2,4-D choline salt (2 parts), glyphosate isopropylamine salt (4 parts), polyoxyethylene steryl phenyl ether (14 parts), calcium dodecylbenzenesulfonate (6 parts), xylene (30 parts) and N,N-dimethylformamide (43.8 parts) are mixed to obtain an emulsifiable concentrate.

Formulation Example 12

Flumioxazin (0.2 parts), 2,4-D choline salt (4 parts), glyphosate isopropylamine salt (2 parts), polyoxyethylene steryl phenyl ether (14 parts), calcium dodecylbenzenesulfonate (6 parts), xylene (30 parts) and N,N-dimethylformamide (43.8 parts) are mixed to obtain an emulsifiable concentrate.

Formulation Example 13

Flumioxazin (0.0625 parts), 2,4-D choline salt (5 parts), glyphosate potassium salt (5 parts), polyoxyethylene steryl phenyl ether (14 parts), calcium dodecylbenzenesulfonate (6 parts), xylene (30 parts) and N,N-dimethylformamide (39.9375 parts) are mixed to obtain an emulsifiable concentrate.

Formulation Example 14

Flumioxazin (0.0625 parts), 2,4-D choline salt (2.5 parts), glyphosate potassium salt (5 parts), polyoxyethylene steryl phenyl ether (14 parts), calcium dodecylbenzenesulfonate (6 parts), xylene (30 parts) and N,N-dimethylformamide (42.4375 parts) are mixed to obtain an emulsifiable concentrate.

Formulation Example 15

Flumioxazin (0.0625 parts), 2,4-D choline salt (5 parts), glyphosate potassium salt (2.5 parts), polyoxyethylene steryl phenyl ether (14 parts), calcium dodecylbenzenesulfonate (6 parts), xylene (30 parts) and N,N-dimethylformamide (42.4375 parts) are mixed to obtain an emulsifiable concentrate.

Formulation Example 16

Flumioxazin (0.0625 parts), 2,4-D choline salt (5 parts), glyphosate isopropylamine salt (5 parts), polyoxyethylene steryl phenyl ether (14 parts), calcium dodecylbenzenesulfonate (6 parts), xylene (30 parts) and N,N-dimethylformamide (39.9375 parts) are mixed to obtain an emulsiliable concentrate.

Formulation Example 17

Flumioxazin (0.0625 parts), 2,4-D choline salt (2.5 parts), glyphosate isopropylamine salt (5 parts), polyoxyethylene steryl phenyl ether (14 parts), calcium dodecylbenzenesulfonate (6 parts), xylene (30 parts) and N,N-dimethylformamide (42.4375 parts) are mixed to obtain an emulsifiable concentrate.

Formulation Example 18

Flumioxazin (0.0625 parts), 2,4-D choline salt (5 parts), glyphosate isopropylamine salt (2.5 parts), polyoxyethylene steryl phenyl ether (14 parts), calcium dodecylbenzenesulfonate (6 parts), xylene (30 parts) and N,N-dimethylformamide (42.4375 parts) are mixed to obtain an emulsifiable concentrate.

Formulation Example 19

Flumioxazin (1 part), 2, 4-D choline salt (2.5 parts), glyphosate potassium salt (2.5 parts), polyoxyethylene steryl phenyl ether (14 parts), calcium dodecylbenzenesulfonate (6 parts), xylene (30 parts) and N,N-dimethylformamide (44 parts) are mixed to obtain an emulsifiable concentrate.

Formulation Example 20

Flumioxazin (1 part), 2,4-D choline salt (1.25 parts), glyphosate potassium salt (2.5 parts), polyoxyethylene steryl phenyl ether (14 parts), calcium dodecylbenzenesulfonate (6 parts), xylene (30 parts) and N,N-dimethylformamide (45.25 parts) are mixed to obtain an emulsifiable concentrate.

Formulation Example 21

Flumioxazin (1 part), 2,4-D choline salt (2.5 parts), glyphosate potassium salt (1.25 parts), polyoxyethylene steryl phenyl ether (14 parts), calcium dodecylbenzenesulfonate (6 parts), xylene (30 parts) and N,N-dimethylformamide (45.25 parts) are mixed to obtain an emulsifiable concentrate.

Formulation Example 22

Flumioxazin (1 part), 2,4-D choline salt (2.5 parts), glyphosate isopropylamine salt (2.5 parts), polyoxyethylene steryl phenyl ether (14 parts), calcium dodecylbenzenesulfonate (6 parts), xylene (30 parts) and N,N-dimethylformamide (44 parts) are mixed to obtain an emulsifiable concentrate.

Formulation Example 23

Flumioxazin (1 part), 2,4-D choline salt (1.25 parts), glyphosate isopropylamine salt (2.5 parts), polyoxyethylene steryl phenyl ether (14 parts), calcium dodecylbenzenesulfonate (6 parts), xylene (30 parts) and N,N-dimethylformamide (45.25 parts) are mixed to obtain an emulsifiable concentrate.

Formulation Example 24

Flumioxazin (1 part), 2,4-D choline salt (2.5 parts), glyphosate isopropylamine salt (1.25 parts), polyoxyethylene steryl phenyl ether (14 parts), calcium dodecylbenzenesulfonate (6 parts), xylene (30 parts) and N,N-dimethylformamide (45.25 parts) are mixed to obtain an emulsifiable concentrate.

[Herbicidal Effect]

The evaluation of the herbicidal effect is classified into 0 to 100, where the numeral "0" indicates no or little difference in the state of germination or growth of test weeds at the time of examination as comparison with untreated weeds and the numeral "100" indicates the complete death of test plants or the complete inhibition of their germination or growth.

Example 1

Plastic pots each filled with soil are seeded with *Amaranthus retroflexus*, *Ipomoea hederacea*, *Echinochloa crusgalli*, and *Digitaria ciliaris*. After seeding, a mixed liquid of flumioxazin and 2,4-D choline salt is uniformly sprayed over a surface of the soil on the day of the seeding. After treatment with the agent, the pots are brought into a green-

Example 2

Plastic pots each filled with soil are seeded with *Amaranthus retroflexus, Ipomoea hederacea, Echinochloa crus-galli*, and *Digitaria ciliaris*. After seeding, a mixed liquid of flumioxazin, 2,4-D choline salt and glyphosate-potassium is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 3

Plastic pots each filled with soil are seeded with *Amaranthus retroflexus, Ipomoea hederacea, Echinochloa crus-galli*, and *Digitaria ciliaris*. After seeding, a mixed liquid of flumioxazin, 2,4-D choline salt and glyphosate isopropylamine salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 4

Plastic pots each filled with soil are seeded with *Amaranthus retroflexus, Ipomoea hederacea, Echinochloa crus-galli*, and *Digitaria ciliaris*. After seeding, a mixed liquid of flumioxazin, 2,4-D choline salt and glyphosate choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 5

Plastic pots each filled with soil are seeded with *Amaranthus retroflexus, Ipomoea hederacea, Echinochloa crus-galli*, and *Digitaria ciliaris*. After seeding, a mixed liquid of sulfentrazone and 2,4-D choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 6

Plastic pots each filled with soil are seeded with *Amaranthus retroflexus, Ipomoea hederacea, Echinochloa crus-galli*, and *Digitaria ciliaris*. After seeding, a mixed liquid of sulfentrazone, 2,4-D choline salt and glyphosate-potassium is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 7

Plastic pots each filled with soil are seeded with *Amaranthus retroflexus, Ipomoea hederacea, Echinochloa crus-galli*, and *Digitaria ciliaris*. After seeding, a mixed liquid of sulfentrazone, 2,4-D choline salt and glyphosate isopropylamine salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 8

Plastic pots each filled with soil are seeded with *Amaranthus retroflexus, Ipomoea hederacea, Echinochloa crus-galli*, and *Digitaria ciliaris*. After seeding, a mixed liquid of sulfentrazone, 2,4-D choline salt and glyphosate choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 9

Plastic pots each filled with soil are seeded with *Amaranthus retrofleuxus, Ipomoea hederacea, Echinochloa crus-galli*, and *Digitaria ciliaris*. After seeding, a mixed liquid of saflufenacil and 2,4-D choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 10

Plastic pots each filled with soil are seeded with *Amaranthus retroflexus, Ipomoea hederacea, Echinochloa crus-galli*, and *Digitaria ciliaris*. After seeding, a mixed liquid of saflufenacil, 2,4-D choline salt and glyphosate-potassium is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 11

Plastic pots each filled with soil are seeded with *Amaranthus retroflexus, Ipomoea hederacea, Echinochloa crus-galli*, and *Digitaria ciliaris*. After seeding, a mixed liquid of saflufenacil, 2,4-D choline salt and glyphosate isopropylamine salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 12

Plastic pots each filled with soil are seeded with *Amaranthus retroflexus, Ipomoea hederacea, Echinochloa crus-galli*, and *Digitaria ciliaris*. After seeding, a mixed liquid of saflufenacil, 2,4-D choline salt and glyphosate choline salt is uniformly sprayed over a surface of the soil on the day of the seeding. After treatment with the agent, the pots are brought into a greenhouse. Fifteen days after treatment with the

Example 13

Plastic pots each filled with soil are seeded with *Amaranthus retroflexus, Ipomoea hederacea, Echinochloa crusgalli,* and *Digitaria ciliaris*. After seeding, a mixed liquid of oxyfluorfen and 2,4-D choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 14

Plastic pots each filled with soil are seeded with *Amaranthus retroflexus, Ipomoea hederacea, Echinochloa crusgalli,* and *Digitaria ciliaris*. After seeding, a mixed liquid of oxyfluorfen, 2,4-D choline salt and glyphosate-potassium is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 15

Plastic pots each filled with soil are seeded with *Amaranthus retroflexus, Ipomoea hederacea, Echinochloa crusgalli,* and *Digitaria ciliaris*. After seeding, a mixed liquid of oxyfluorfen, 2,4-D choline salt and glyphosate isopropylamine salt is uniformly sprayed over a surface of the soil on the day of the seeding. After treatment with the agent, the pots are brought into a green house. Fifteen days after treatment with the agent, pots are seeded with soybean, field corn and cotton. As a result, an excellent herbicidal effect is found.

Example 16

Plastic pots each filled with soil are seeded with *Amaranthus retroflexus, Ipomoea hederacea, Echinochloa crusgalli,* and *Digitaria ciliaris*. After seeding, a mixed liquid of oxyfluorfen, 2,4-D choline salt, and glyphosate choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 17

Plastic pots each filled with soil are seeded with *Amaranthus retroflexus, Ipomoea hederacea, Echinochloa crusgalli,* and *Digitaria ciliaris*. After seeding, a mixed liquid of fomesafen-sodium and 2,4-D choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 18

Plastic pots each filled with soil are seeded with *Amaranthus retroflexus, Ipomoea hederacea, Echinochloa crusgalli,* and *Digitaria ciliaris*. After seeding, a mixed liquid of fomesafen-sodium, 2,4-D choline salt and glyphosate-potassium is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 19

Plastic pots each filled with soil are seeded with *Amaranthus retroflexus, Ipomoea hederacea, Echinochloa crusgalli,* and *Digitaria ciliaris*. After seeding, a mixed liquid of fomesafen-sodium, 2,4-D choline salt and glyphosate isopropylamine salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 20

Plastic pots each filled with soil are seeded with *Amaranthus retroflexus, Ipomoea hederacea, Echinochloa crusgalli,* and *Digitaria ciliaris*. After seeding, a mixed liquid of fomesafen-sodium, 2,4-D choline salt and glyphosate choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 21

Plastic pots each filled with soil are seeded with *Amaranthus retroflexus, Ipomoea hederacea, Echinochloa crusgalli,* and *Digitaria ciliaris*. After seeding, a mixed liquid of Compound 1 and 2,4-D choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 22

Plastic pots each filled with soil are seeded with *Amaranthus retroflexus, Ipomoea hederacea, Echinochloa crusgalli,* and *Digitaria ciliaris*. After seeding, a mixed liquid of Compound 1, 2,4-D choline salt and glyphosate-potassium is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 23

Plastic pots each filled with soil are seeded with *Amaranthus retroflexus, Ipomoea hederacea, Echinochloa crusgalli,* and *Digitaria ciliaris*. After seeding, a mixed liquid of Compound 1, 2,4-D choline salt and glyphosate isopropylamine salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

Example 24

Plastic pots each filled with soil are seeded with *Amaranthus retroflexus, Ipomoea hederacea, Echinochloa crusgalli,* and *Digitaria ciliaris.* After seeding, a mixed liquid of Compound 1, 2,4-D choline salt and glyphosate choline salt is uniformly sprayed over a surface of the soil on the day of the seeding. After treatment with the agent, the pots are brought into a greenhouse. Fifteen days after treatment with the agent, pots are seeded with soybean, field corn and cotton. As a result, an excellent herbicidal effect is found.

According to the present invention, it is possible to control weeds in a crop field, a vegetable field, a tree land, a non-cultivated land, or the like.

What is claimed is:

1. A herbicidal composition comprising flumioxazin and 2,4-D choline salt,
   wherein the weight ratio of flumioxazin to 2,4-D choline salt is from 1:2.5 to 1:20.

2. A method for controlling weeds, comprising applying flumioxazin and 2,4-D choline salt to weeds or soil in a place where the weeds grow or will grow,
   wherein the weight ratio of flumioxazin to 2,4-D choline salt is from 1:2.5 to 1:20.

3. The method according to claim 2, wherein the place where the weeds grow or will grow is a soybean field, a cotton field, or a corn field.

4. The method according to claim 3, wherein a soybean in the soybean field, cotton in the cotton field or corn in the corn field is a genetically-modified soybean, genetically-modified cotton or genetically-modified corn.

5. The method according to claim 3, wherein a soybean in the soybean field, cotton in the cotton field or corn in the corn field is a herbicide-resistant genetically-modified soybean, herbicide-resistant genetically-modified cotton or herbicide-resistant genetically-modified corn.

6. The method according to claim 3, wherein a soybean in the soybean field or cotton in the cotton field is a 2,4-D-resistant genetically-modified soybean or 2,4-D-resistant genetically-modified cotton.

* * * * *